United States Patent [19]
Koch et al.

[11] Patent Number: 4,929,243
[45] Date of Patent: May 29, 1990

[54] CATHETER COUPLING

[75] Inventors: Heinrich Koch, Lichtenau; Jügen Fuchs, Emstal-Sand, both of Fed. Rep. of Germany

[73] Assignee: B. Braun Melsungen AG, Melsungen, Fed. Rep. of Germany

[21] Appl. No.: 301,438

[22] Filed: Jan. 25, 1989

[30] Foreign Application Priority Data

Feb. 9, 1988 [DE] Fed. Rep. of Germany ....... 8801583

[51] Int. Cl.$^5$ ............................................. A61M 25/02
[52] U.S. Cl. ..................................... 604/283; 604/905
[58] Field of Search ........................ 604/280, 283, 905; 285/356

[56] References Cited

U.S. PATENT DOCUMENTS

| 2,332,354 | 10/1943 | Stecher | 285/356 |
| 2,782,058 | 2/1957 | Clingman et al. | 285/356 |
| 3,469,579 | 6/1969 | Hubert | 604/283 |
| 3,802,433 | 4/1974 | Raven | 604/283 |
| 4,187,848 | 2/1980 | Taylor | 604/280 |
| 4,191,185 | 3/1980 | Lemieux | 604/283 |
| 4,252,122 | 2/1981 | Halvorsen | 604/905 |
| 4,391,029 | 7/1983 | Czuba et al. | 604/283 |
| 4,547,194 | 10/1985 | Moorehead | 604/905 |
| 4,621,841 | 11/1986 | Wakefield | 285/356 |
| 4,820,283 | 4/1989 | Schickling et al. | 604/280 |

FOREIGN PATENT DOCUMENTS 3102142 8/1982 Fed. Rep. of Germany .
3644916 4/1988 Fed. Rep. of Germany .

Primary Examiner—Dalton L. Truluck
Assistant Examiner—Denise W. DeFranco
Attorney, Agent, or Firm—Spensley Horn Jubas & Lubitz

[57] ABSTRACT

A catheter coupling is provided with a hollow connecting member on which a thrust element can be screwed. The head of an elastomeric clamping member sits in the cavity of the connecting member. A tubular projection extends from the head through the thrust element. The catheter is pushed over a supporting cannula. As the thrust element is tightened, the head is crushed above the catheter and the projection is twisted. Crushing and torsion reduce the inner diameter of the clamping member, so that it fits around the catheter and seals it. This results in a long seal. The clamping member is connected with the thrust piece, so that the entire catheter coupling requires handling of only two parts.

6 Claims, 1 Drawing Sheet

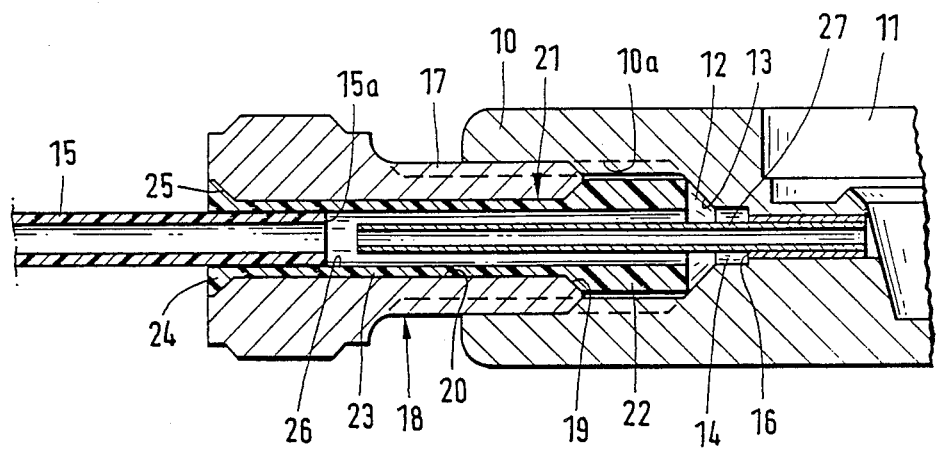

CATHETER COUPLING

BACKGROUND OF THE INVENTION

1. Field of the Invention

The invention relates to a catheter coupling.

2. Description of Related Art

A connection housing of a known catheter coupling (German Pat. No. 31 02 142) is provided with a hollow connecting member, into which the catheter can be inserted. Inside the connecting member, an elastomeric clamping member is arranged, having a channel for the passage of the catheter. When a thrust element is screwed on the connecting member, the clamping member is axially compressed by the thrust element (provided as a swivel nut), whereby the thrust element is radially deformed and whereby it fixes the catheter in the connecting member. The axial pressure reduces the diameter of the channel in the clamping member, which causes a crushing of the clamping member around the catheter. This known catheter coupling is safe only if hard and dimensionally stable tubes are used as catheters. Softer tubes would be compressed, so that the catheter lumen would be reduced without, however, arriving at the desired connection of tensile strength. Due to the limited length of the clamping member, the catheter is only compressed and fixed over a range of a few millimeters at its proximal end. This can lead to leaking of the catheter coupling, especially if the catheter consists of a comparatively soft material.

A further disadvantage of the known catheter coupling is the fact that the elastomeric clamping member could fall out of the connecting member with the thrust element being screwed off. In practical use, the connecting member and the clamping member are often threaded on the catheter separately to be jointly mounted on the connection housing. This threading is particularly difficult with catheters of a small lumen and correspondingly small bores.

It is an object of the present invention to provide a catheter coupling of the kind that can be easily handled without problems and that makes a secure sealing between the catheter and the connecting member possible over a longer range.

SUMMARY OF THE INVENTION

In accordance with the present invention, these and other objectives are achieved by providing a catheter coupling having a clamping member. The clamping member of the catheter coupling according to the present invention is axially crushed and radially deformed at the screwing on of the thrust element, and is provided with an axial projection extending into the channel of the thrust element.

When the thrust element is screwed on, not only the head of the clamping member is compressed, but also the projection of the clamping member is twisted, since the clamping member is mounted on the connecting member and turns with it and since, on the other hand, it is also in frictional contact with the peripheral surface of the catheter. This torsional deforming also reduces the diameter of the clamping member projection, so that the catheter is not only radially pressed at the head of the clamping member, but also at the clamping member projection, which is located inside the channel of the thrust element. This substantially increases the length of the catheter that is compressed from outside and the length of the catheter passage sealed. Further, an increased tensile stability of the catheter coupling is achieved. Moreover, the mounting of the clamping member on the thrust element represents a fixed mutual coordination of both parts, so that the catheter coupling consists of only two parts to be screwed together. At least before use the clamping member is a part of the thrust element.

The clamping member can be fastened to the thrust element, e.g., by injection, gluing, clamping or by interlocking. In some applications it is advantageous that the hold of the connection is sufficiently low, so that the clamping member is torn off the thrust element at the screwing on of the latter. When the catheter is coupled on, i.e., when the thrust element is screwed to the connecting member, the head of the clamping member settles firmly on the preferably conical pressure receiving shoulder of the connecting member. This compresses and crushes the head of the clamping member. It cannot follow further turns of the thrust element and is detached from it. The tubular projection of the clamping member is also detached from the thrust element, so that the torsional force acting on the catheter is limited.

In one embodiment of the present invention a support cannula may be provided to achieve, on the one hand, the catheter's security against collapsing and, on the other hand, to fix it so that it cannot turn with the clamping member or the projection.

BRIEF DESCRIPTION OF THE DRAWINGS

A detailed description of a preferred embodiment of the invention will be made with reference to the accompanying drawing.

FIG. 1 shows a longitudinal section of the catheter coupling in a relaxed state during the insertion of the catheter end.

DESCRIPTION OF THE PREFERRED EMBODIMENT

The following detailed description is of the best presently contemplated mode of carrying out the invention. This description is not to be taken in a limiting sense, but is made merely for the purpose of illustrating the general principles of the invention. The scope of the invention is best defined by the appended claims.

As illustrated in FIG. 1, the catheter coupling is provided with a connecting member 10 that, in the preferred embodiment, is part of a housing 11, from which a fluid pharmaceutic can be lead into a patient's body via the catheter. The catheter coupling can also be provided at another device to be connected, e.g., a syringe or a connecting member that is connected to a tube.

The connecting member 10 is provided with a cavity 12, which in this case is a threaded bore, the thread bearing the reference numeral 10a. The inner limit of the cavity 12 is defined by an inclined pressure receiving shoulder 13. The pressure receiving shoulder ends in the cylindrical receiving space 14, the diameter of which is adapted to the outer diameter of the catheter 15 and that is provided with an abutment shoulder 16 for the catheter end 15a.

The thread 17 of the thrust element 18 is screwed into the thread 10a of the connecting member 10. The end of the thread shaft of the thrust element 18 is provided with a pressure receiving shoulder 19 of the male cone type. A channel 20 extends over the whole length of the thrust element 18.

The elastomeric clamping member 21 is provided with a head 22, one end of which is mounted on the pressure receiving shoulder 19 and which forms an axial extension of the thrust element 18. The other end of the head 22 abuts against the pressure receiving shoulder 13 of the connecting member 10. The tubular projection 23 of the clamping member 21 extends from the head 22 through the channel 20. The outer end of the projection 23 is provided with a conical enlargement 24, which is located in a corresponding recess 25 of the thrust element 18. The axial channel 26 of the clamping member 21 extends over the whole length of the clamping member with a constant crosssection.

Mounted on the housing 11 or the connecting member 10 is a supporting cannula 27 of rigid material, e.g., steel, which protrudes axially into the cavity 12 and the free end of which protrudes beyond the end of the connecting member 10. The outer diameter of the supporting cannula 27 corresponds approximately to the inner diameter of the catheter 15, so that the catheter 15 can be pushed on the supporting cannula 27 until its end 15a hits the meeting shoulder 16, without having to overcome any substantial frictional forces.

The clamping member 21 is injection molded onto the thrust element 18, the pressure receiving shoulder 19 and the wall of the channel 20 providing adhesion surfaces.

The mounting of the catheter coupling on the catheter 15 is done by unscrewing the thrust element 18 from the connecting member 10 and pushing the thrust element 18 on the catheter 15. Then the catheter 15 is inserted into the connecting member 10 via the supporting cannula 27. Subsequently, the thrust element 18, together with the clamping member 21 mounted thereon, is inserted into the cavity 12 and screwed to the connecting member 10.

The head 22 of the clamping member, in its relaxed state, can be freely advanced axially into the inner thread. Upon further tightening of the thrust element 18, the head 22 is crushed between the pressure receiving shoulders 19 and 13, so that the head is enlarged radially outward and inward, with the friction at the connecting member 10 steadily increasing. Subsequently, the adhesion between the clamping member 21 and the pressure receiving shoulder 19 is interrupted. The projection 23 of the clamping member 21 is twisted, so that the projection 23 is constricted and fits tightly around the outside of the catheter 15. Finally, the adhesion between the projection 23 and the wall of the channel 20 is interrupted. The catheter 15 is thereby supported on the supporting cannula 27 and prevented by friction from turning.

The connection, thus provided, between the connecting member 10 and the catheter 15 is of a relatively high tensile strength, which generally exceeds the tenacity of the catheter 15.

The clamping member 21 can also be fastened to the thrust element 18 by fitting the pre-molded clamping member into the channel 20 of the thrust element using correspondent static friction. Thus, the thrust element and the clamping member can be produced separately and can be assembled to mate without gluing or welding.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A catheter coupling comprising:
   a connecting member having a cavity and configured to receive an end of the catheter,
   a thrust element having a pressure receiving shoulder and being configured to extend into the connecting member and defining a channel for the catheter, and
   a compressible clamping member affixed to the thrust element, the clamping member having a head and a substantially tubular projection attached to the channel of the thrust element, the head having an outer diameter and the tubular projection having an outer diameter, the outer diameter of the head being greater than the outer diameter of the tubular projection, the tubular projection extending beyond the pressure receiving shoulder in the channel of the thrust element,
   whereby the head is compressed axially and the projection is deformed radially when the thrust element extends into the connecting member.

2. A catheter coupling comprising:
   a connecting member having a cavity and configured to receive an end of the catheter,
   a thrust element having a pressure receiving shoulder and configured to extend into the connecting member and defining a channel for the catheter,
   a compressible clamping member affixed to the thrust element, the clamping member having a substantially tubular projection attached to the channel of the thrust element, the tubular projection extending beyond the pressure receiving shoulder in the channel of the thrust element, and
   means for establishing surface friction between the clamping member and the catheter and between the clamping member and the connecting member, whereby relative rotation of the connecting member and the thrust element extending into the connecting member will detach the tubular projection from the channel of the thrust element.

3. A catheter coupling according to claim 1, further comprising:
   a supporting cannula attached to the connecting member and extending through the cavity of the connecting member, the supporting cannula being adapted for sliding the catheter end thereon.

4. A catheter coupling according to claim 1, wherein the projection of the clamping member extends substantially over the entire length of the channel of the thrust element.

5. A catheter coupling according to claim 1, wherein the fixing area of the clamping member extends at least partly over the length of the projection.

6. A catheter coupling according to claim 1, further comprising:
   detachment means for detaching the tubular projection and the thrust element, the detachment means including
   means for establishing relative rotation of the connecting member and the thrust element extending into the connecting member,
   means for establishing surface friction between the clamping member and the catheter, and
   means for establishing surface friction between the clamping member and the connecting member,
   whereby relative rotation of the connecting member and the thrust element extending into the connecting member detaches the tubular projection and the thrust element.

* * * * *